United States Patent
Chattopadhyay et al.

(10) Patent No.: US 6,372,922 B1
(45) Date of Patent: Apr. 16, 2002

(54) PROCESS FOR THE PRODUCTION OF (−) 3,4-DIVANILLYL TETRAHYDROFURAN

(75) Inventors: Sunil Kumar Chattopadhyay; Sachin Srivastava; Vinayak Tripathi, all of Uttar Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/818,278

(22) Filed: Mar. 27, 2001

(51) Int. Cl.$^7$ ............................................. C07D 307/12
(52) U.S. Cl. ........................................................ 549/502
(58) Field of Search ......................................... 549/502

(56) References Cited

U.S. PATENT DOCUMENTS 4,977,146 A * 12/1990 Biftu et al. .................... 514/99
5,300,658 A * 4/1994 Frank et al. ................. 549/502

OTHER PUBLICATIONS

Schottner, M., et al. "Lignans from the Roots of *Urtica dioica* and their Metabolites Bind to Human Sex Hormome Binding Globulin (SHBG) "*Planta Medica*, vol. 63, pp. 529–532, (1997).

Mujumdar, R. B., et al. "Taxiresinol, A New Lignan in the Heartwood of *Taxus baccata*"*Indian Journal of Chemistry*, vol. 10, pp. 677–680, (1972).

Barry, C. N., et al. "Triphenylphosphine–Tetrachloromethane Promoted Chlorination and Cyclodehydration of Simple Diols"*J. Org. Chem.*, vol. 46, pp. 3361–3364, (1981).

Lin, Long–Ze, et al. "Lycorine Alkaloids from *Hymenocallis Littoralis*"*Phytochemistry*, vol. 40, pp. 1295–1298, (1995).

* cited by examiner

*Primary Examiner*—Ba K. Trinh
(74) *Attorney, Agent, or Firm*—Ladas & Parry

(57) ABSTRACT

The present invention relates to a process for the production of (−)3,4-divanillyl tetrahydrofiran of formula (2) which comprises (a) isolating) (−) secoisolariciresinol of formula (1) from the heartwood and roots of *Taxus wallichiana* by an improved process which consists of partitioning of the alcoholic extract of the heartwood and roots of *T. wallichiana* between water and chlorinated solvent, (b) extracting the chlorinated solvent extract with alkali and (c) isolating (−) secoisolariciresinol from the alkali extract upon neutralization with mineral acid and extracting with organic solvent and (d) crystallizing it from suitable organic solvent, (e) dissolving the isolated (−) secoisolariciresinol in suitable organic solvent and (f) reacting with triphenyl phosphine halide at 0–80° C. for 1–10 hours and (g) isolating (−) 3,4-divanillyl tetrahydrofuran by column chromatography.

22 Claims, No Drawings

PROCESS FOR THE PRODUCTION OF (−) 3, 4-DIVANILLYL TETRAHYDROFURAN

FIELD OF THE INVENTION

This invention relates to a process for the production of (−) 3,4-divanillyl tetrahydrofuran. More particularly, this invention relates to an improved process for the isolation of (−) secoisolariciresinol from the heart wood and roots of *Taxus wallichiana* and conversion of (−) secoisolariciresinol of formula (1) into its semisynthetic analog (−) 3,4-divanillyl tetrahydrofuran of formula (2).

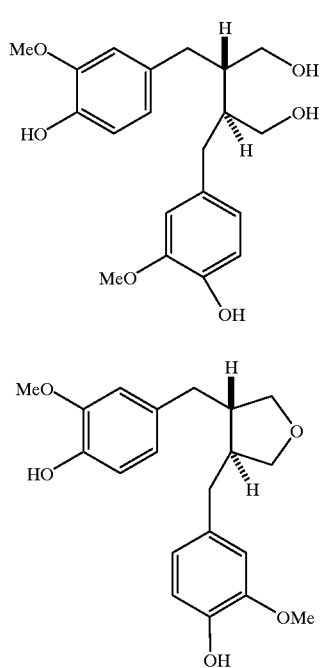

BACKGROUND OF THE INVENTION (−) secoisolariciresinol is a known molecule and it has previously been isolated from the heartwood of *T. wallichiana* but it has never been isolated from, the roots of *T. wallichiana*. According to a prior art process, (−) secoisolariciresinol has been isolated from the heartwood of *T. wallichiana* consists of extracting the powdered heartwood with cold methanol and concentrating the methanol to get methanol extract, treating the methanol extract with hot petroleum-ether to remove waxes and subjecting the dewaxed material to counter current distribution process between equal volumes of benzene, ethyl acetate, water, methanol yielding three main fractions, subjecting the desired fraction containing (−) secoisolariciresinol to column chromatography and isolating (−) secoisolariciresinol from the column by eluting with benzene acetone as eluent with a yield of 0.1% (Taxiresinol, a new lignan in the heartwood of *Taxus baccata* [R. B. Mujumdar, R. Srinivasan and K. Venkataraman, Indian J. Chem 10, 677–680 (1972)].

The process described above for the isolation of (−) secoisolariciresinol from *T. wallichina* suffers from several disadvantages which include, extra step of defatting with petroleum ether, use of benzene (which is carcinogenic) as a solvent both in the counter current distribution process and also as a eluent during isolating from the column and the use-of column chromatography which makes the process tedious, time consuming and required extra volumes of solvents.

According to another prior art process, the preparation of (−) 3,4-divanillyl tetrahydrofuran of formula (2) from (−) secoisolariciresinol of formula (1) involves the treatment of (−) secoisolariciresinol in an acetone solution with perchloric acid. The drawback of the process includes that the epoxide of formula (2) thus formed is unstable in acidic solution and it gets partly decomposed to the starting material i.e. (−) secoisolariciresinol of formula (I).

The plant *Taxus wallichiana* is an important plant from the medicinal point of view as it contains the anticancer compound paclitaxel (=taxol®) in it. Paclitaxel, a highly oxygenated diterpenoid molecule and a potent anticancer drug for the treatments of ovarian and breast cancers, was first isolated from *Taxus brevifolia*. Thereafter, it has also been isolated from the Himalayan yew *Taxus wallichiana*. We have been working on different parts-stem bark, needles, heartwood, roots and seeds of *T. wallichiana* as a part of our systematic investigation on the plant for the isolation of paclitaxel, its important analogs, precursors and other biologically active molecules. During the course of this investigation, we have been able to isolate an important molecule (−) secoisolariciresinol of formula (1) from the heartwood as well as roots of this plant with high yields.

Recent findings have established that (−) secoisolariciresinol possesses significant aromatase inhibition property. Aromatase is a key enzyme in steroid hormone metabolism. It mediates the conversion of androgens into estrogens. Aromatase is of considerable therapeutic interest since estrogen production has been associated with endometrial and breast cancers. Aromatase inhibitors are used in treating estrogen dependent breast cancers.

(−) secoisolariciresinol is also capable of reducing the binding of 3H-labelled 5a-dihydro testosterone (DHT) to human sex hormone binding globulin (SHBG) and thereby reduces the chance of growth of prostate cancer. However, the semisynthetic analog (−) 3,4-divanillyl tetrahydrofuran prepared from (−) secoisolariciresinol by the process of the invention is more active in reducing the bindina of $^3$H-labelled 5a-dihydro testosterone (DHT) to human sex hormone binding globulin (SHBG). Thus (−) 3,4-divanillyl tetrahydrofuran is more active than (−) secoisolariciresinol in reducing the chance of growth of prostate cancers in human.

OBJECTS OF THE INVENTION

The object of the present invention is to develop an improved process for isolation of (−) secoisolariciresinol from the heartwood and roots of *T. wallichiana* with high yields.

Another object of the present invention is to develop a processing technology for the isolation of (−) secoisolariciresinol from the heartwood and roots of *T. wallichiana* which does not use any chromatographic separation for its isolation.

Yet another object of the present invention is to avoid the use of carcinogenic solvent benzene for isolation of (−) secoisolariciresinol.

Still another object of the present invention is to convert (−)secoisolariciresinol of formula (1) into its more active semisynthetic analog (−) 3,4divanillyl tetrahydrofuran of formula (2) under neutral condition.

Yet another object of the present invention is to convert (−) secoisolariciresinol into (−) 3,4-divanillyl tetrahydrofuran with high yields.

SUMMARY OF THE INVENTION

In order to overcome the drawbacks of the prior art processes, we have developed a simple and practical process for production of (−) 3,4,-divanillyl tetrahydrofuran of formula (2)

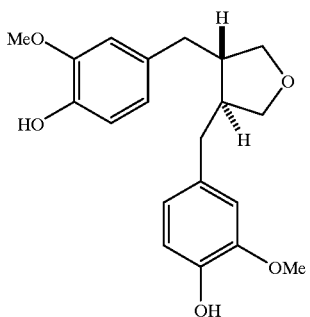

(2)

comprising (a) extracting the pulverized heartwood/roots of *T. wallichiana* with alcohol at ambient temperature and concentrating the solvent furnished an alcoholic extract, (b) treating the alcoholic extract with water and extracting with a chlorinated solvent exhaustively (c) concentrating the chlorinated solvent to a residue and treating the residue with aqueous solution of a base and extracting the alkaline layer with an organic solvent (d) neutralizing the aqueous alkaline solution with mineral acid and extracting with an organic solvent (e) concentrating the organic solvent to a residue and crystallizing it from a suitable organic solvent or mixture of such solvents to get (−) secoisolariciresiniol of formula (1),

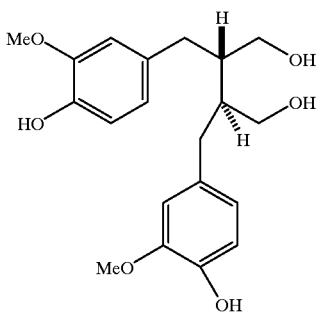

(1)

(f) dissolving the isolated (−) secoisolariciresinol in an organic solvent and reacting it with triphenyl phosphine halide at 0–80° C. for 1–10 hours and (g) isolating (−) 3,4-divanillyl tetrahydrofuran of formula (2) by column chromatography.

Accordingly the present invention relates to a process for the preparation of (−) 3,4-divanillyl tetrahydrofuran of formula (2), said process comprising (f) dissolving the isolated (−) secoisolariciresinol in an organic solvent, reacting it with triphenyl phosphine halide at 0–80° C. for 1–10 hours and (g) isolating (−) 3,4-divanillyl tetrahydrofuran of formula (2) by column chromatography.

In one embodiment of the present invention the alcohol used in step (a) is an alkanol selected from the group consisting of methanol and ethanol.

In another embodiment of the invention, the chlorinated solvent in step (b) is selected from the group consisting of chloroform and dichloromethane.

In yet another embodiment of the invention, the base used in step (c) is selected from the group consisting of sodium hydroxide, potassium hydroxide and lithium hydroxide.

In a further embodiment of the present invention, the organic solvent used in step (c) is selected from the group consisting of toluene chloroform, dichloromethane and ethyl acetate.

In yet another embodiment of the present invention, the mineral acid in step (d) is selected from the group consisting of hydrochloric acid and sulphuric acid.

In yet another embodiment of the invention, the suitable organic solvent or mixtures of such solvents used in step (e) is selected from the group consisting of acetone, and mixtures of acetone-petroleum ether, acetone-hexane, ethyl acetate-pet.ether and ethylacetate-hexane.

In another embodiment of the invention, the organic solvent used in step (f) for dissolving (−) secoisolariciresinol, is selected from the group consisting of acetonitrile, methanol, tetrahydrofuran, chloroform and dichloromethane.

In a yet another embodiment of the present invention, the triphenyl phosphine halide used in step (f) is selected from a group consisting of triphenyl phosphine bromide and triphenylphosphine chloride.

In a further embodiment of the present invention, the column chromatography used in step (g) is selected from a group consisting of silica gel, florosil, alumina and celite.

DETAILED DESCRIPTION OF THE INVENTION

The process of the invention for the isolation of (−) secoisolariciresinol from the heartwood and roots of *T. wallichiana* does not use column chromatography. The improved isolation process comprises (a) extracting the pulverized heartwoods/roots of *T. wallichiana* with an alcohol at ambient temperature and concentrating the solvent to obtain an alcoholic extract, (b) treating the alcoholic extract with water and extracting it with chlorinated solvents exhaustively (c) concentrating the chlorinated solvent to a residue and treating the resultant residue with aqueous solution of a base and extracting the alkaline layer with an organic solvent (d) neutralizing the alkaline solution with mineral acid and extracting with an organic solvent, (e) concentrating the organic solvent to a residue and crystallizing it from a suitable organic solvent or mixtures of such solvents to get (−) secoisolariciresinol of formula (1).

The isolated (−) secoisolariciresinol of formula (1) is converted into (−) 3,4-divanillyl tetrahydrofuran of formula (2) by (f) dissolving the isolated (−) secoisolariciresinol in an organic solvent, reacting it with triphenyl phosphine halide at 0–80° C. for 1–10 hours and (g) isolating (−) 3,4-divanillyl tetrahydrofuran of formula (2) by column chromatography.

The alcohol used in step (a) can be an alkanol such as methanol and ethanol. The chlorinated solvent in step (b) is selected from the group consisting of chloroform and dichloromethane. The base used in step (c) is selected from the group consisting of sodium hydroxide, potassium hydroxide and lithium hydroxide.

The organic solvent used in step (c) is selected from the group consisting of toluene, chloroform, dichloromethane, ethyl acetate. The mineral acid in step (d) is selected from the group consisting of hydrochloric acid, sulphuric acid. The suitable organic solvent or mixtures of such solvents used in step (e) comprises acetone, and mixtures of acetone-petroleum ether acetone-hexane, ethyl acetate-pet.ether, ethylacetate-hexane or any mixture thereof.

The organic solvent used in step (f) for dissolving (−) secoisolariciresinol, is selected from the group consisting of acetonitrile, methanol, tetrahydrofuran, chloroform, dichloromethane. The triphenyl phosphine halide used in step (f) is selected from a group consisting of triphenyl phosphine bromide, triphenylphosphine chloride.

The column chromatography used in step (g) is selected from a group consisting of silica gel, florosil, alumina, celite.

The invention is described in detail in the examples given below which are provided to illustrate the invention and therefore should not be construed to limit the scope of the invention.

EXAMPLE I

Production of(-) Secoisolariciresinol From Heartwood

Air dried pulverized heartwood (1 kg) of *T. wallichiana* were extracted with MeOH (5 lit×3) at ambient temperature for three days. MeOH extract was concentrated to a residue and the residue was treated with water (2 liter) and extracted with $CHCl_3$ (3 lit×3) exhaustively. The $CHCl_3$ was concentrated under vacuum and the residue thus obtained was dissolved in 1N NaOH solution (1 lit) with stirring and extracted with $CHCl_3$ (1 lit×3). The aqueous NaOH layer was neutralized with 1N HCl and extracted with ethylacetate (1 lit×3). The ethyl acetate layer was washed with water, dried over anhydrous sodium sulphate and concentrated to a residue which crystallized out and filtered. It was recrystallized from a mixture of acetone-pet. ether to give (-) secoisolariciresinol (2 g) mp. 112–113° C., $[\alpha]_D$–25° (Cl, MeOH).

EXAMPLE II

Production of (-) Secoisolariciresinol From Roots

Air dried, pulverized roots (1 kg) were extracted and processed as per process given in example I to give (-) secoisolariciresinol m.p. 112–113° C., $[\alpha]_D$-25° (Cl, MeOH), yield 2.01 g.

EXAMPLE III

Production of (-) Secoisolariciresinol From Heartwood

Air dried pulverized heartwood (1 kg) of *T. wallichiana* were extracted with EtOH (5 lit×3) at ambient temperature for three days. EtOH extract was concentrated to a residue and the residue was treated with water (2 liter) and extracted with $CH_2Cl_2$ (3 lit×3) exhaustively. The $CH_2Cl_2$ extract was concentrated under vacuum and the residue thus obtained was dissolved in 1N KOH solution (1 lit) with stirring and extracted with $CH_2Cl_2$ (1 lit×3). The aqueous KOH layer was neutralized with 1N $H_2SO_4$ and extracted with $CHCl_3$, (2 lit×3). $CHCl_3$ layer was washed with water, dried over anhydrous sodium sulphate and concentrated to give a residue which crystallized out and filtered. It was recrystallized from a mixture of acetone-hexane to give (-) secoisolariciresinol (2 g) mp. 112–113° C., $[\alpha]_D$–25° (Cl, MeOH).

EXAMPLE IV

Production of (-) Secoisolariciresinol From Roots

Air dried, pulverized roots (1 kg) were extracted and processed as per process given in example III to give (-) secoisolariciresinol, mp. 112–113° C., $[\alpha]_D$–25° (Cl, MeOH), yield (2.01 g).

EXAMPLE V

Production of (-) 3,4-divanillyl Tetrahydrofuran (-) secoisolariciresinol (100 mg) was dissolved in acetonitrile (5 ml) and to it was added a solution of triphenyl phosphine bromide in acetonitrile (1 ml) and the mixture was stirred at 0–80° C. for 1–10 hours. After completion of the reaction, the reaction mixture was concentrated under vacuum and the residue thus obtained was chromatographed over silica gel column. Elution of the column with 30% EtOAC in pet. ether gave (-) 3,4-divanillyl tetrahydrofuran (78 mg), m.p. 114–116° C.

EXAMPLE VI

Production of (-) 3,4-divanillyl Tetrahydrofuran (-) secoisolariciresinol (100 mg,) was dissolved in THF (5 ml) and to it was added a solution of triphenyl phosphine chloride in acetonitrile (1 ml) and the mixture was stirred at 0–80° C. for 1–10 hours. After completion of the reaction, the reaction mixture was concentrated under vacuum and the residue thus obtained was chromatographed over florosil column. Elution of the column with 30% EtOAC in pet. ether gave (--3,4-divanillyl tetrahydrofuran (77 mg), m.p. 114–116° C.

Advantages

1. The process developed for isolation of (-) secoisolariciresinol from the heartwood/roots of *T. wallichiana* is simple, practical and straightforward. No extreme conditions are necessary for its isolation.
2. The process developed for isolation of (-) secoisolariciresinol did not need any chromatographic separation. Thus, the process is cost effective and viable for commercial production.
3. The solvent that would be used for extraction can be recycled and thus the process would be cost effective.
4. Compared to prior art process, (-) 3,4-divanillyl tetrahydrofuran has been prepared from (-) secoisolariciresinol under neutral condition and thereby excellent yield (90%) has been obtained for the compound.
5. The yields of (-) secoisolariciresinol and (-) 3,4-divanillyl tetrahydrofiran obtained by the process of the present invention has been compared with the corresponding yield reported earlier.

| Source | (-) secoiso-lariciresinol | (-) 3,4 divanillyl tetrahydrofuran |
|---|---|---|
| *Taxus wallichiana* (heartwood) | 0.1% | — |
| Previous art | — | No yield reported (However, 40% yield obtained following the prior art process) |
| Present process | 0.2% | >90% |

We claim:

1. A process for production of (-)3,4-divanillyl tetrahydrofuran of formula (2) (2)

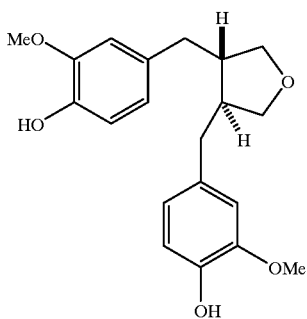

(2)

said process comprising (a) extracting the pulverized heartwoods/roots of *T. wallichiana* with an alcohol at ambient temperature and concentrating the solvent to obtain an alcoholic extract, (b) treating the alcoholic extract with water and extracting it with a chlorinated solvent exhaustively (c) concentrating the chlorinated solvent to a residue and treating the resultant residue with aqueous solution of a base and extracting the alkaline layer with an organic solvent (d) neutralizing the alkaline solution with mineral acid and extracting with an organic solvent, (e) concentrating the organic solvent to a residue and crystallizing it from a suitable organic solvent or mixtures of such solvents to get (−) secoisolariciresinol of formula (1)

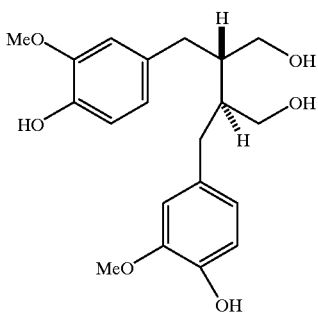

(1)

(f) dissolving the isolated (−) secoisolariciresinol in an organic solvent, reacting it with triphenyl phosphine halide at 0–80° C. for 1–10 hours and (g) isolating (−) 3,4-divanillyl tetrahydrofuran of formula (2) by column chromatography.

2. A process as claimed in claim 1 wherein the alcohol used in step (a) is an alkanol selected from the group consisting of methanol and ethanol.

3. A process as claimed in claim 2 wherein the alcohol is methanol.

4. A process as claimed in claim 1 wherein the chlorinated solvent used in step (b) is selected from chloroform and dichloromethane.

5. A process as claimed in claim 4 wherein the chlorinated solvent is chloroform.

6. A process as claimed in claim 1 wherein the base used in step (c) is selected from the group consisting of sodium hydroxide, potassium hydroxide and lithium hydroxide.

7. A process as claimed in claim 6 wherein the base is sodium hydroxide.

8. A process as claimed in claim 1 wherein the organic solvent used to extract the alkaline layer in step (c) is selected from the group consisting of toluene, chloroform, dichloromethane and ethyl acetate.

9. A process as claimed in claim 8 wherein the organic solvent is chloroform.

10. A process as claimed in claim 1 wherein the mineral acid used in step (d) to neutralize the alkaline solution is selected from hydrochloric acid and sulphuric acid.

11. A process as claimed in claim 10 wherein the mineral is hydrochloric acid.

12. A process as claimed in claim 1 wherein the organic solvent used in step (d) to extract the neutral solution is selected from the group consisting ethylacetate, chloroform and dichloromethane.

13. A process as claimed in claim 12 wherein the organic solvent is ethylacetate.

14. A process as claimed in claim 1 wherein the suitable organic solvent or mixtures of such solvent used in step (e) to crystallize (−) secoisolariciresinol is selected from the group consisting of acetone, and mixtures of acetone-petroleum ether, acetone-hexane, ethyl acetate-pet. Ether and ethylacetate-hexane.

15. A process as claimed in claim 14 wherein the mixture of solvent is acetone petroleum ether.

16. A process as claimed in claim 1 wherein the organic solvent used in step (f) for dissolving (−) secoisolariciresinol, is selected from the group consisting of acetonitrile, methanol, tetrahydrofuran, chloroform and dichloromethane.

17. A process as claimed in claim 16 wherein the solvent is acetonitrile.

18. A process as claimed in claim 1 wherein the triphenyl phosphine halide used in step (f) is selected from triphenyl phosphine bromide and triphenylphosphine chloride.

19. A process as claimed in claim 18 wherein the triphenyl phosphine halide is triphenyl phosphine bromide.

20. A process as claimed in claim 1 wherein the temperature is 60° C. and the time period of the reaction in step (f) is 2 hours.

21. A process as claimed in claim 1 wherein the column chromatography used in step (g) to purify (−) 3 4-divanillyl tetrahydrofuran is selected from the group consisting of silica gel, florosil, alumina and celite.

22. A process as claimed in claim 21 wherein the column chromatography comprises of silica gel.

* * * * *